US009610287B2

(12) United States Patent
Holm et al.

(10) Patent No.: US 9,610,287 B2
(45) Date of Patent: Apr. 4, 2017

(54) METHOD OF ADMINISTRATION OF 4-((1R,3S)-6-CHLORO-3-PHENYL-INDAN-1-YL)-1,2,2-TRIMETHYL-PIPERAZINE AND THE SALTS THEREOF IN THE TREATMENT OF SCHIZOPHRENIA

(75) Inventors: René Holm, Jyllinge (DK); Lone Bruun, Solrød Strand (DK)

(73) Assignee: H. Lundbeck A/S, Valby (DK)

( * ) Notice: Subject to any disclaimer, the term of this patent is extended or adjusted under 35 U.S.C. 154(b) by 57 days.

(21) Appl. No.: 14/126,499

(22) PCT Filed: Jun. 20, 2012

(86) PCT No.: PCT/EP2012/061779
§ 371 (c)(1),
(2), (4) Date: Mar. 14, 2014

(87) PCT Pub. No.: WO2012/175531
PCT Pub. Date: Dec. 27, 2012

(65) Prior Publication Data
US 2014/0194409 A1 Jul. 10, 2014

Related U.S. Application Data

(60) Provisional application No. 61/498,653, filed on Jun. 20, 2011.

(30) Foreign Application Priority Data

Jun. 20, 2011  (DK) ................................ 2011 00465

(51) Int. Cl.
A61K 31/495 (2006.01)
A61K 31/5513 (2006.01)
A61K 31/4545 (2006.01)
A61K 31/554 (2006.01)
A61K 31/496 (2006.01)
A61K 31/4515 (2006.01)
A61K 31/454 (2006.01)
A61K 31/517 (2006.01)
A61K 31/519 (2006.01)

(52) U.S. Cl.
CPC .......... A61K 31/495 (2013.01); A61K 31/454 (2013.01); A61K 31/4515 (2013.01); A61K 31/4545 (2013.01); A61K 31/496 (2013.01); A61K 31/517 (2013.01); A61K 31/519 (2013.01); A61K 31/554 (2013.01); A61K 31/5513 (2013.01)

(58) Field of Classification Search
CPC ............. A61K 31/495; A61K 31/4515; A61K 31/454; A61K 31/4545; A61K 31/496; A61K 31/517; A61K 31/519; A61K 31/5513; A61K 31/554
See application file for complete search history.

(56) References Cited

U.S. PATENT DOCUMENTS 7,767,683 B2   8/2010  Lopez de Diego et al.
8,076,342 B2   12/2011 Lopez de Diego et al.
8,227,607 B2   7/2012  de Diego et al.

FOREIGN PATENT DOCUMENTS

| RU | 2006140962 A  | 11/2006 |
| WO | 2005102342 A1 | 11/2005 |
| WO | 2007011955 A2 | 1/2007  |
| WO | 2009135495 A1 | 11/2009 |
| WO | 2010/037398 A1| 4/2010  |
| WO | 2010037398 A1 | 4/2010  |
| WO | 2010149727 A2 | 6/2010  |

OTHER PUBLICATIONS

International Search Report and Written Opinion issued Jul. 26, 2012 in International Application No. PCT/EP2012/061779.
Anonymous, Mar. 23, 2010, "Zicronapine", New Drugs Online, XP002680825, Retrieved from the Internet: URL: http://www.ukmi.nhs.uk/applications/ndo/record_view_open.asp?newDrugID=5028 [retrieved on Jul. 26, 2012].
Clozapine Augmentation Article, Graylands Hospital Drug Bulletin 2004, vol. 12 No. 1, March ISSN 123-1251, Claramont, WA, 6 pages.
Kito et al., "The Rehospitalization-reducing Effect of Supporting Self-administration According to Individual Cognitive Function of Patients with Schizophrenia", Nippon Byolin Yakuzaishikai, vol. 46, No. 8, pp. 1114-1117 (2010).
New Pharmacology, 3rd revised edition, pp. 20-21, 268-278.
Goff et al., "Once-weekly D-cycloserine effects on negative symptoms and cognition in schizophrenia: An exploratory study", Schizophrenia Research, vol. 106, pp. 320-327 (2008).
Kane et al., "A Double-Blind, Randomized Study Comparing the Efficacy and Safety of Sertindole and Risperidone in Patients with Treatment-Resistant Schizophrenia", J. Clin. Psychiatry, vol. 72, No. 2, pp. 194-204 (2011).
Manual of Diagnosis and Therapy, vol. II, Editor in Chief, Robert Berkow, D.M., pp. 57-65 (1997).
"The clinical phase III programme commenced on zicronapine", Corporate Release No. 423, 3 pages, (2011).
Chemistry Database, Compound Summary for CID 11465618 Zicronapine.
New Drugs Online XP-002680825, Online Report for Zicronapine.
Japanese Office Action dated Dec. 20, 2016 issued in corresponding Japanese application.
Partial English language translation of New General Pharmaceutics, Revised Third Edition, pp. 262-267 (1987).
New General Pharmaceutics, Revised Third Edition, pp. 262-267 (1987).

Primary Examiner — Sarah Pihonak
Assistant Examiner — Jason A Deck
(74) Attorney, Agent, or Firm — Morgan, Lewis & Bockius, LLP

(57) ABSTRACT

The present invention relates to 4-((1R,3S)-6-chloro-3-phenyl-indan-1-yl)-1,2,2-trimethyl-piperazine and the salts thereof with activity at dopamine $D_1$ and $D_2$ receptors as well as the serotonin $5HT_2$ receptor for the treatment of diseases in the central nervous system in a once weekly dosing regime.

7 Claims, 1 Drawing Sheet

Panel 1  Study Design
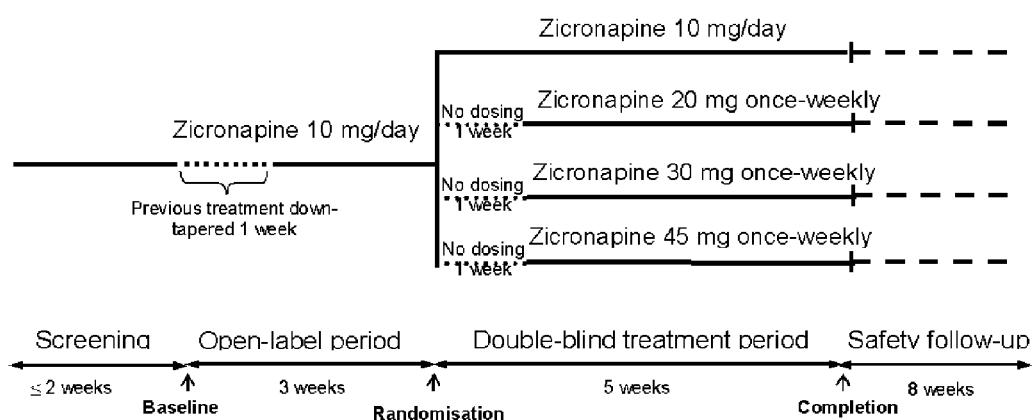

METHOD OF ADMINISTRATION OF 4-((1R,3S)-6-CHLORO-3-PHENYL-INDAN-1-YL)-1,2,2-TRIMETHYL-PIPERAZINE AND THE SALTS THEREOF IN THE TREATMENT OF SCHIZOPHRENIA

CROSS-REFERENCE TO RELATED APPLICATIONS

The present application is a National Stage Application which claims priority of International Application No. PCT/EP12/061779, filed Jun. 20, 2012, which claims priority of U.S. Provisional Application No. 61/498,653, filed Jun. 20, 2011 and Danish Application No. PA201100465, filed Jun. 20, 2011. Each of these applications is hereby incorporated by reference in its entirety.

FIELD OF THE INVENTION

The present invention relates to 4-((1R,3S)-6-chloro-3-phenyl-indan-1-yl)-1,2,2-trimethyl-piperazine and the salts thereof with activity at dopamine $D_1$ and $D_2$ receptors as well as the serotonin $5HT_2$ receptor for the treatment of diseases in the central nervous system in a once weekly dosing regime.

BACKGROUND OF THE INVENTION 4-((1R,3S)-6-chloro-3-phenyl-indan-1-yl)-1,2,2-trimethyl-piperazine and the salts thereof, pharmaceutical compositions containing these salts and the medical use thereof, including treatment of schizophrenia or other diseases involving psychotic symptoms, is disclosed in WO2005/016900. 4-((1R,3S)-6-chloro-3-phenyl-indan-1-yl)-1,2,2-trimethyl-piperazine is hereinafter referred to as Compound (I)

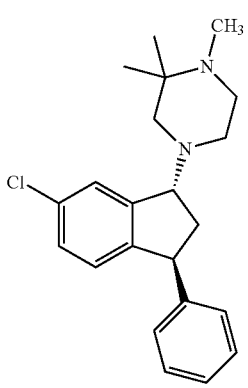

(I)

Compound (I) is also known as Zicronapine.

EP 638 073 covers a group of trans isomers of 3-aryl-1-(1-piperazinyl)indanes substituted in the 2- and/or 3-position of the piperazine ring. The compounds are described as having high affinity for dopamine $D_1$ and $D_2$ receptors and the $5-HT_2$ receptor and are suggested to be useful for treatment of several diseases in the central nervous system, including schizophrenia.

Compound (I) above has been described by Bøgesø et al. in *J. Med. Chem.*, 1995, 38, page 4380-4392, in the form of the fumarate salt, see table 5, compound (−)-38. This publication concludes that the (−)-enantiomers of compound 38 is a potent $D_1/D_2$ antagonists showing some $D_1$ selectivity in vitro. The compound is also described as a potent $5-HT_2$ antagonist. It is also mentioned that the compound does not induce catalepsy in rats.

The aetiology of schizophrenia is not known, but the dopamine hypothesis of schizophrenia formulated in the early 1960s, has provided a theoretical framework for understanding the biological mechanisms underlying this disorder (Carlsson, *Am. J. Psychiatry* 1978, 135, 164-173). In its simplest form, the dopamine hypothesis states that schizophrenia is associated with a hyperdopaminergic state, a notion which is supported by the fact that all antipsychotic drugs on the market today exert some dopamine $D_2$ receptor antagonism (Seeman *Science and Medicine* 1995, 2, 28-37). However, whereas it is generally accepted that antagonism of dopamine $D_2$ receptors in the limbic regions of the brain plays a key role in the treatment of positive symptoms of schizophrenia, the blockade of $D_2$ receptors in striatal regions of the brain causes extrapyramidal symptoms (EPS). As described in EP 638 073 a profile of mixed dopamine $D_1/D_2$ receptor inhibition has been observed with some so-called "atypical" antipsychotic compounds, in particular with clozapine (8-chloro-11-(4-methylpiperazin-1-yl)-5H-dibenzo[b,e][1,4] diazepine), used in treatment of schizophrenic patients.

Further, selective $D_1$ antagonists have been connected to treatment of sleep disorders and alcohol abuse (D. N. Eder, *Current Opinion in Investigational Drugs*, 2002 3(2):284-288).

Dopamine may also play an important role in the aetiology of affective disorders (P. Willner, *Brain. Res. Rev.* 1983, 6, 211-224, 225-236 and 237-246; Bøgesø et al, *J. Med. Chem.*, 1985, 28, 1817-1828).

In EP 638 073 is described how compounds having affinity for $5-HT_2$ receptors, in particular $5-HT_{2A}$ receptor antagonists, have been suggested for treatment of different diseases, such as schizophrenia including the negative symptoms in schizophrenic patients, depression, anxiety, sleep disturbance, migraine attacks and neuroleptic-induced parkinsonism. $5-HT_{2A}$ receptor antagonism has also been suggested to reduce the incidence of extrapyramidal side effects induced by classical neuroleptics (Balsara et al. *Psychopharmacology* 1979, 62, 67-69).

Psychotic patients, and in particular schizophrenic patients, are often unwilling or unable to take their medication regularly; several studies have shown that a less frequent dosing results in higher degree of compliance and thus eventually better treatment of the patients. Therefore there is an unmet need for long acting preparations of antipsychotic medicine. In particular there is a need for long acting preparations of antipsychotic medicine in non-invasive form that represent an alternative to intra muscular depot formulations in order to make change in dosing regime, frequency of medication or type of medication, more flexible.

SUMMARY OF THE INVENTION

The inventors of the present invention have surprisingly found that the elimination half life of Compound (I) in human is about 150 hours. The long elimination half life in combination with affinity for both dopamine D1 and D2 receptors makes Compound (I) a putative long acting antipsychotic compound that can be administered weekly, biweekly or semiweekly in e.g. a non-invasive form, such as in an instant release formulation (IR-formulation), an extended, controlled or a delayed release formulation for oral administration.

Further, the inventors of the present invention have surprisingly found that the main metabolite of Compound (I) in human, namely trans-1(6-chloro-3-phenyl-indan-1-yl)-3,3-dimethyl-piperazine, Compound (II), and which also possesses affinity for both dopamine D1 and D2 receptors, has an elimination half life of about 300-400 hours.

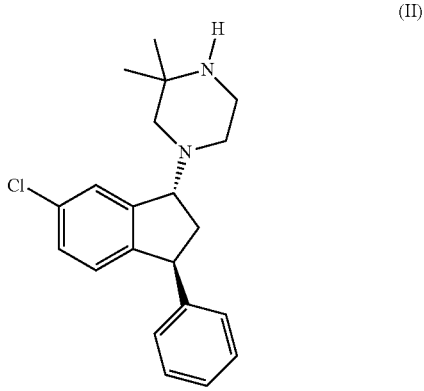 [SMILES: CC1(C)CN([C@@H]2C[C@@H](c3ccccc3)c3ccc(Cl)cc32)CCN1]

(II)

This surprising combination of a long half life and affinity for both dopamine D1 and D2 receptors for Compound (I) and its main metabolite has lead the inventors of present invention to conclude that Compound (I) may be administered with a longer time interval than usually in the treatment of psychosis. Accordingly, it is anticipated that Compound (I) can be administered once weekly, twice weekly (semi-weekly), or every second week (biweekly) in maintenance treatment of psychosis as well as in the treatment of acute exacerbation in psychosis.

The inventors of the present application have surprisingly found that dosing Compound (I) once weekly at a dose between about 30 mg/week and about 45 mg/week reduces the PANSS Total Score at least to the same extend as a daily dose of 10 mg/day. This allows for lower doses to be administered to humans i.e. less burden to the entire body, e.g. the liver, and a less frequent dosing.

BRIEF DESCRIPTION OF THE FIGURES

FIG. 1 shows the study design applied for once weekly dosing of Compound (I)

DETAILED DESCRIPTION OF THE INVENTION

As already indicated Compound (I) is a putative antipsychotic compound with affinity for both dopamine D1 and D2 receptors. Preclinical experiments in rats using the condition avoidance response (CAR) model (Experimental procedure previously described in: Hertel P, Olsen C K, Arnt J., *Eur. J. Pharmacol.* 2002; 439(1-3):107-11.) have indicated that Compound (I) possesses antipsychotic activity at very low levels of D2 receptor occupancy.

In a positron emission tomography (PET) study in healthy subjects using $^{11}$C-SCH23390 and $^{11}$C-raclopride as D1 and D2 receptor tracers, it was found that Compound (I) induces a D2 receptor occupancy of from 11 to 43% in the putamen when increasing the dose from 2 to 10 mg/day given daily for 18 days. Such level of D2 receptor occupancy is low in comparison with that of currently used antipsychotic drugs, which in general requires a D2 receptor occupancy around or exceeding 50% to be therapeutically effective (Stone J M, Davis J M, Leucht S, Pilowsky L S. *Schizophr Bull.* 2008 Feb. 26). In the same PET study, it was found that Compound (I) induces a D1 receptor occupancy increase from 32 to 69% in putamen when increasing the dose from 2 to 10 mg/day given daily for 18 days. Such high level of D1 occupancy is not generally seen with current used antipsychotic drugs (Farde L, Nordstrom A L, Wiese F A, Pauli S, Halldin C, Sedvall G. *Arch Gen Psychiatry.* 1992; 49(7): 538-44.). Thus, Compound (I) exhibits a unique ratio of D1 to D2 receptor occupancy.

Based on the above, it is expected that Compound (I) has clinically significant therapeutic effects in patients with schizophrenia at doses (from 4 mg/dose to 60 mg/dose) that induce only a low level of D2 receptor occupancy. This might well be a consequence of the high D1 receptor occupancy and the unique ratio of D1 versus D2 receptor occupancy displayed by Compound (I). A low D2 receptor occupancy at therapeutically effective doses will be beneficial in terms of reduced tendency to induce troublesome side effects mediated by D2 receptor blockade, including extrapyramidal side effects and hyperprolactinemia.

Compound (I) in a therapeutically effective amount of from 4-60 mg calculated as the free base is administered orally, and may be presented in any form suitable for such administration, e.g. in the form of tablets, capsules, powders, syrups or solutions.

In one embodiment, a salt of Compound (I) is administered in the form of a solid pharmaceutical entity, suitably as a tablet, such as an orally disintegrating tablet, or a capsule.

Pharmaceutically Acceptable Salts

The present invention also comprises salts of Compound (I), typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, the contents of which are hereby incorporated by reference.

Furthermore, Compound (I) of this invention and salts thereof may exist in unsolvated as well as in solvated forms with pharmaceutically acceptable solvents such as water, ethanol and the like. In general, the solvated forms are considered comparable to the unsolvated forms for the purposes of this invention.

In a particular embodiment of the present invention Compound (I) is in the form of a succinate salt or a malonate salt.

Pharmaceutical Compositions

The present invention further provides a pharmaceutical composition comprising a therapeutically effective amount of Compound (I) of the present invention and a pharmaceutically acceptable carrier or diluent.

Compound (I) of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

In a particular embodiment the pharmaceutical composition comprising Compound (I) disintegrates within 15 minutes, in particular within 10 minutes, such as 5 minutes, 4 minutes, 3 minutes, 2 minutes or 1 minute, as measured according to the procedure described in Remington's Pharmaceutical Sciences, 18$^{th}$ edition (Ed. A. R. Genaro), 1990, pp. 1640-1641.

The pharmaceutical compositions may be specifically formulated for administration by any suitable route such as oral, nasal, topical (including buccal and sublingual), and parenteral (including subcutaneous, intramuscular, intrathecal, intravenous and intradermal) routes. It will be appreciated that the route will depend on the general condition and age of the subject to be treated, the nature of the condition to be treated and the active ingredient.

Compound (I) of this invention is generally utilized as the free substance or as a pharmaceutically acceptable salt thereof. Examples of suitable organic and inorganic acids are described above.

Dosing Regime

Long acting antipsychotic compound, long acting preparations, and long acting preparations of antipsychotic compounds refer to compounds and preparations of compounds that maintain pharmaceutically active levels of the exogenously administered compound for more than one day, such as for a week, so that the compound need not to be given on a daily basis but semiweekly, weekly or even biweekly.

The present invention relates to Compound (I) for the treatment of a disease in the central nervous system, including psychosis, in particular schizophrenia or other diseases involving psychotic symptoms, such as, e.g. Schizophreniform Disorder, Schizoaffective Disorder, Delusional Disorder, Brief Psychotic Disorder, Shared Psychotic Disorder as well other psychotic disorders or diseases that present with psychotic symptoms, e.g. bipolar disorder, such as mania in bipolar disorder, wherein Compound (I) is administered semiweekly, weekly or biweekly.

The invention also relates to a method for the medical use of Compound (I), such as for the treatment of a disease in the central nervous system, including psychosis, in particular schizophrenia or other diseases involving psychotic symptoms, such as, e.g. Schizophreniform Disorder, Schizoaffective Disorder, Delusional Disorder, Brief Psychotic Disorder, Shared Psychotic Disorder as well other psychotic disorders or diseases that present with psychotic symptoms, e.g. bipolar disorder, such as mania in bipolar disorder, wherein Compound (I) is administered semiweekly, weekly or biweekly.

The weekly (i.e. with an interval of 7 days) or semiweekly (i.e. twice a week with a 3 to 4 days interval) or biweekly (i.e. with and interval of 14 days) dose of Compound (I), calculated as the free base, is suitably between 1 mg/dose and 100 mg/dose, more suitable between 1 mg/dose and 60 mg/dose, e.g. preferably between 5 mg/dose and 55 mg/dose, such as between 10 mg/dose and 45 mg/dose mg, in particular between 30 mg/dose and 45 mg/dose, such as 40 ring/dose or 45 ring/dose.

Accordingly, in a specific embodiment the invention relates to Compound (I) for the treatment of a disease in the central nervous system, characterized in that Compound (I) is administered semiweekly, weekly or biweekly in a dose corresponding to between 20 mg/week and 50 mg/week calculated as the free base of Compound (I)

The weekly, semiweekly (i.e. twice a week with a 3 to 4 days interval) or biweekly (i.e. with and interval of 14 days) administration of Compound (I) may be for the maintenance treatment of a disease in the central nervous system, in particular psychosis, as well as for the treatment of acute exacerbation in psychosis.

Maintenance treatment is designed to prevent relapse once patients have been stabilized by either Compound (I) of the present invention or by a different anti-psychotic compound.

Acute exacerbation is a sudden worsening of the psychotic conditions.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 10 percent up or down (higher or lower).

As used herein the term "between" used in conjunction with a numerical range includes the lower and upper value (the end points) of the range.

The use of the terms "a" and "an" and "the" and similar referents in the context of describing the invention are to be construed to cover both the singular and the plural, unless otherwise indicated herein or clearly contradicted by context.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

EXPERIMENTAL

Binding Assays

Description of Human $D_2$ Binding Assay

The assay can be performed as a SPA-based competition-binding in a 50 mM Tris pH 7.4 assay buffer containing 120 mM NaCl, 5 mM KCl, 4 mM $MgCl_2$, 1.5 mM $CaCl_2$, 1 mM EDTA.

1.5 nM $^3$H-raclopride (Perkin Elmer, NET 975) is mixed with test compound before addition of 20 microg of a homogenised human $D_2$ receptor membrane-preparation and 0.25 mg SPA beads (WGA RPNQ 0001, Amersham) in a total volume of 90 microL. The assay plates are under agitation incubated for 60 minutes at room temperature and subsequently counted in a scintillation counter (TriLux, Wallac). The total binding, which comprised approximately 15% of added radioligand, is defined using assay buffer, whereas the non-specific binding is defined in the presence of 10 microM haloperidol. The non-specific binding constituted approximately 10% of the total binding.

Data points are expressed in percent of the specific binding of $^3$H-Raclopride and the $IC_{50}$ values (concentration causing 50 percent inhibition of $^3$H-raclopride specific binding) are determined by non-linear regression analysis using a sigmoidal variable slope curve fitting. The dissociation constant ($K_i$) is calculated from the Cheng Prusoff equation ($K_i=IC_{50}/(1+(L/K_D))$), where the concentration of free radioligand L is approximated to the concentration of added $^3$H-raclopride in the assay. The $K_D$ of $^3$H-raclopride is determined to 1.5 nM from two independent saturation assays each performed with triplicate determinations.

Description of Human $D_1$ Binding Assay

The assay is performed as a SPA-based competition-binding in a 50 mM Tris pH 7.4 assay buffer containing 120 mM NaCl, 5 mM KCl, 4 mM $MgCl_2$, 1.5 mM $CaCl_2$, 1 mM EDTA. Approximately 1 nM $^3$H-SCH23390 (Perkin Elmer, NET 930) is mixed with test compound before addition of 2.5 microg of a homogenized human $D_1$ receptor membrane-preparation and 0.25 mg SPA beads (WGA RPNQ 0001, Amersham) in a total volume of 60 microL.

The assay plates are under agitation incubated for 60 minutes at room temperature before the plates are centrifuged and subsequently counted in a scintillation counter (TriLux, Wallac). The total binding, which comprised approximately 15% of added radioligand, is defined using assay buffer whereas the non-specific binding is defined in the presence of 10 microM haloperidol.

Data points are expressed in percent of the specific binding and the $IC_{50}$ values (concentration causing 50 percent inhibition of specific binding) and are determined by non-linear regression analysis using a sigmoidal variable slope curve fitting. The dissociation constant ($K_i$) is calculated from the Cheng Prusoff equation ($K_i=IC_{50}/(1+(L/K_D))$), where the concentration of free radioligand L is approximated to the concentration of added radio-ligand in the assay.

Description of Human 5-$HT2_A$ Binding

The experiment is carried out at Cerep Contract Laboratories (Cat. ref. #471).

Description of In Vivo Binding to $D_2$ Receptors in Rat Brain

In vivo binding is carried out according to Andersen et al (Eur J Pharmacol, (1987) 144:1-6) with a few modifications (Kapur S. et al, J Pharm Exp Ther, 2003, 305, 625-631). Briefly, 6 rats (male Wistar, 180-200 g) are treated with 20 mg/kg test compound subcutaneous 30 minutes before receiving 9.4 micro Ci [$^3$H]-raclopride intravenous via the tail vein.

15 minutes after the injection of the radio ligand the animals are killed by cervical dislocation, the brain quickly removed and striatum and cerebellum dissected out and homogenized in 5 mL (cerebellum in 20 mL) ice-cold buffer (50 mM $K_2PO_4$, pH 7.4). 1.0 mL of the homogenate is filtered through 0.1% PEI—soaked Whatman GF/C filters. This is completed within 60 seconds subsequent to the decapitation. Filters are washed 2 times with 5 mL ice-cold buffer and counted in a scintillation counter. A group of vehicle treated animals is used to determine [$^3$H]-raclopride total binding in striatum and non-specific binding in cerebellum. The homogenate is measured for protein content by the BCA protein determination assay (Smith P. K. et al (1985) Anal. Biochem., 150: 6-85).

Example 1

Binding Affinity of Compound (I)

Previously conducted in vitro binding studies have shown that Compound (I) binds to the D1, $D_2$ and 5-$HT_2A$ receptors with the following affinities:
Human $D_1$ binding: $K_i$=19 nM
Human 5-$HT2_A$ binding: $K_i$=4.2 nM
In vivo binding to $D_2$ receptors in brain: $ED_{50}$=4.1 mg/kg Example 2

Study Design

The design of the study that was conducted to evaluate the feasibility of a once weekly dosing of Compound (I), administered in the form of hydrogen succinate salt of Compound (I), is out-lined in FIG. 1. The study is a randomized, double-blind, parallel-group, exploratory study of safety, tolerability and PK of daily dosing vs weekly dosing of Compound (I) in schizophrenic patients.

The open-label period (OL_Period) is the period from start of open-label treatment (baseline) until stop of open-label treatment (at OL-withdrawal or randomisation to double-blind treatment, whichever occurs first).

The placebo period (PBO_Period) is the first week of double-blind treatment where patients randomised to weekly dosing receive placebo treatment, while patients randomised to daily dosing continue treatment with 10 mg/day Compound (I)

The double-blind period (DB_Period) is the period from start of double-blind treatment (randomisation) until stop of double-blind treatment (at DB-withdrawal or completion, whichever occurs first), that is, the entire double-blind period including the PBO_Period.

The IMP dosing period (IMP_Period) is the period from start of open-label treatment (baseline) until stop of double-blind treatment (at withdrawal or completion, whichever occurs first), that is, the OL_Period plus the DB_Period.

Example 3

Changes from Randomization in PANSS Total Score

A study was conducted with a study design as described in Example 2.

Results as changes from randomization in PANSS Total Score are provided in table 1:

TABLE 1

| Treatment group | Study day | N | Mean (change in PANSS) |
|---|---|---|---|
| Compound (I) 10 mg/day | 29 | 11 | 1.55 |
| | 36 | 10 | −1.00 |
| | 43 | 10 | −2.50 |
| | 50 | 10 | −3.50 |
| | 57 | 10 | −5.80 |
| Compound (I) 20 mg/week | 29 | 10 | 0.00 |
| | 36 | 10 | 0.80 |
| | 43 | 8 | −2.00 |
| | 50 | 9 | −1.22 |
| | 57 | 8 | −4.38 |
| Compound (I) 30 mg/week | 29 | 11 | 1.09 |
| | 36 | 10 | 0.50 |
| | 43 | 8 | 4.00 |
| | 50 | 7 | −4.14 |
| | 57 | 7 | −5.43 |
| Compound (I) 45 mg/week | 29 | 10 | 0.40 |
| | 36 | 10 | −3.50 |
| | 43 | 10 | −5.70 |
| | 50 | 10 | −8.00 |
| | 57 | 8 | −6.88 |

The above data shows that once weekly dosing in the range of 20 mg/week to 45 mg/week, in particular 30 mg/week and 45 mg/week, is as effective in reduction in PANSS Total Score as a daily dose of 10 mg/day.

The invention claimed is:

1. A method of treating a patient suffering from a psychosis, comprising administering Compound (I) weekly in a single oral dose corresponding to between 20 mg/week and 50 mg/week calculated as the free base of Compound (I), wherein Compound (I) is wherein the psychosis is schizophrenia.

2. The method of claim 1 wherein Compound (I) is administered in combination with one or more neuroleptic agents.

3. The method of claim 2 wherein the neuroleptic agent is selected from the group consisting of sertindole, olanzapine, risperidone, quetiapine, aripiprazole, haloperidol, clozapine, ziprasidone and osanetant.

4. The method of claim 1, wherein Compound (I) is administered in a single oral dose of between 20 mg and 50 mg per week.

5. The method of claim 4, wherein Compound (I) is administered in a single oral dose of between 30 mg and 45 mg per week.

6. The method of claim 5, wherein Compound (I) is administered in a single oral dose of about 30 mg per week.

7. The method of claim 5, wherein Compound (I) is administered in a single oral dose of about 45 mg per week.

* * * * *